United States Patent
Bruneau et al.

(10) Patent No.: US 8,012,179 B2
(45) Date of Patent: Sep. 6, 2011

(54) DYNAMIC SPINAL STABILIZATION MEMBERS AND METHODS

(75) Inventors: Aurelien Bruneau, Memphis, TN (US); Thomas Carls, Memphis, TN (US); Eric C. Lange, Collierville, TN (US); John D. Pond, Jr., Germantown, TN (US); Kent Anderson, Memphis, TN (US); Henry Bonin, Memphis, TN (US)

(73) Assignee: Warsaw Orthopedic, Inc., Warsaw, IN (US)

( * ) Notice: Subject to any disclaimer, the term of this patent is extended or adjusted under 35 U.S.C. 154(b) by 1194 days.

(21) Appl. No.: 11/429,816

(22) Filed: May 8, 2006

(65) Prior Publication Data

US 2007/0270836 A1    Nov. 22, 2007

(51) Int. Cl.
*A61B 17/70* (2006.01)
*A61B 17/56* (2006.01)

(52) U.S. Cl. ............... 606/257; 606/246; 606/70

(58) Field of Classification Search .......... 606/246–279, 606/280–299, 70–71; 623/17.11–17.16
See application file for complete search history.

(56) References Cited

U.S. PATENT DOCUMENTS

| | | | |
|---|---|---|---|
| 4,361,141 A | 11/1982 | Tanner | |
| 4,771,767 A | 9/1988 | Steffee | |
| 4,854,304 A | 8/1989 | Zielke | |
| 5,154,718 A | 10/1992 | Cozad et al. | |
| 5,217,461 A | 6/1993 | Asher et al. | |
| 5,330,472 A | 7/1994 | Metz-Stavenhagen | |
| 5,330,474 A | 7/1994 | Lin | |
| 5,336,223 A | 8/1994 | Rogers | |
| 5,403,314 A | 4/1995 | Currier | |
| 5,425,732 A | 6/1995 | Ulrich | |
| 5,486,174 A | 1/1996 | Fournet-Fayard et al. | |
| 5,540,688 A | 7/1996 | Navas | |
| 5,562,660 A | 10/1996 | Grob | |
| 5,575,790 A | 11/1996 | Chen et al. | |
| 5,593,408 A | 1/1997 | Gayet et al. | |
| 5,630,816 A | 5/1997 | Kambin | |
| 5,704,936 A | 1/1998 | Mazel | |
| 5,725,582 A * | 3/1998 | Bevan et al. ................. 606/263 |
| 6,099,528 A | 8/2000 | Saurat | |
| 6,102,912 A | 8/2000 | Cazin et al. | |
| 6,162,223 A * | 12/2000 | Orsak et al. ................. 606/59 |
| 6,241,730 B1 * | 6/2001 | Alby ........................... 606/256 |
| 6,248,106 B1 * | 6/2001 | Ferree ......................... 606/263 |
| 6,296,644 B1 | 10/2001 | Saurat et al. | |

(Continued)

FOREIGN PATENT DOCUMENTS

EP    0 612 507 A1    2/1994

*Primary Examiner* — Thomas C Barrett
*Assistant Examiner* — Matthew Lawson

(57) ABSTRACT

Devices and methods for spinal stabilization include first and second anchor assemblies engageable to respective ones of first and second vertebrae and a connecting element engageable to the first and second anchor assemblies. The connecting element includes opposite first and second anchor engaging end portions and a length along a longitudinal axis between the first and second anchor engaging end portions sized for positioning between and engaging each of the first and second anchor assemblies when the first and second anchor assemblies are engaged to the respective vertebrae. The connecting element further includes a support portion between the first and second anchor engaging end portions. The support portion includes first and second support members spaced from one another on opposite sides of the longitudinal axis, and a stabilizing member extending between the support members in a transverse orientation to the longitudinal axis.

20 Claims, 3 Drawing Sheets

U.S. PATENT DOCUMENTS

| | | | |
|---|---|---|---|
| 6,440,169 B1 * | 8/2002 | Elberg et al. | 623/17.16 |
| 6,626,944 B1 * | 9/2003 | Taylor | 623/17.16 |
| 6,761,720 B1 * | 7/2004 | Senegas | 606/249 |
| 6,802,844 B2 | 10/2004 | Ferree | |
| 6,966,910 B2 * | 11/2005 | Ritland | 606/257 |
| 7,297,146 B2 * | 11/2007 | Braun et al. | 606/279 |
| 7,442,208 B2 * | 10/2008 | Mathieu et al. | 623/17.11 |
| 7,520,887 B2 * | 4/2009 | Maxy et al. | 606/248 |
| 7,524,324 B2 * | 4/2009 | Winslow et al. | 606/248 |
| 7,553,320 B2 * | 6/2009 | Molz et al. | 606/247 |
| 7,585,316 B2 * | 9/2009 | Trieu | 606/279 |
| 7,641,673 B2 * | 1/2010 | Le Couedic et al. | 606/259 |
| 2002/0133155 A1 | 9/2002 | Ferree | |
| 2003/0093078 A1 | 5/2003 | Ritland | |
| 2003/0171749 A1 * | 9/2003 | Le Couedic et al. | 606/61 |
| 2003/0191470 A1 * | 10/2003 | Ritland | 606/61 |
| 2004/0002708 A1 * | 1/2004 | Ritland | 606/61 |
| 2004/0049189 A1 | 3/2004 | Le Couedic et al. | |
| 2004/0049190 A1 | 3/2004 | Biedermann et al. | |
| 2004/0073215 A1 | 4/2004 | Carli | |
| 2004/0143264 A1 | 7/2004 | McAfee | |
| 2004/0215191 A1 | 10/2004 | Kitchen | |
| 2004/0215192 A1 | 10/2004 | Justis et al. | |
| 2005/0010220 A1 | 1/2005 | Casutt et al. | |
| 2005/0131407 A1 | 6/2005 | Sicvol et al. | |
| 2005/0171539 A1 * | 8/2005 | Braun et al. | 606/61 |
| 2005/0182401 A1 | 8/2005 | Timm et al. | |
| 2005/0203514 A1 | 9/2005 | Jahng et al. | |
| 2005/0203519 A1 | 9/2005 | Harms et al. | |
| 2005/0261685 A1 | 11/2005 | Fortin et al. | |
| 2005/0277922 A1 | 12/2005 | Trieu et al. | |
| 2005/0288672 A1 | 12/2005 | Ferree | |
| 2006/0009768 A1 | 1/2006 | Ritland | |
| 2006/0036240 A1 | 2/2006 | Colleran et al. | |
| 2006/0084994 A1 | 4/2006 | Atkinson et al. | |
| 2006/0106381 A1 | 5/2006 | Ferree et al. | |
| 2006/0129239 A1 * | 6/2006 | Kwak | 623/17.13 |
| 2006/0149238 A1 | 7/2006 | Sherman et al. | |
| 2006/0184171 A1 * | 8/2006 | Biedermann et al. | 606/61 |
| 2006/0229608 A1 * | 10/2006 | Foster et al. | 606/61 |
| 2007/0016193 A1 * | 1/2007 | Ritland | 606/61 |
| 2007/0073289 A1 * | 3/2007 | Kwak et al. | 606/61 |
| 2007/0233074 A1 * | 10/2007 | Anderson et al. | 606/61 |

* cited by examiner

DYNAMIC SPINAL STABILIZATION MEMBERS AND METHODS

BACKGROUND

Elongated connecting elements, such as rods, plates, tethers, wires, cables, and other devices have been implanted along the spinal column and connected between two or more anchors engaged between one or more spinal motion segments. Such connecting elements can provide a rigid construct that resists movement of the spinal motion segment in response to spinal loading or movement of the spinal motion segment by the patient. Other connecting elements can resist loading or movement of the spinal motion segment that creates a tension force on the connecting element; however, the connecting element collapses in response to any compression loading and provides little or no resistance in response to such forces or movement. Still other connecting elements are flexible to permit at least limited spinal motion while providing resistance to loading and motion of the spinal motion segment that is the same in both compression and tension.

While prior connecting elements provide various spinal stabilization options, there remains a need for connecting elements that can provide variable resistance properties to forces and motion in different directions along the spinal motion segment for dynamic stabilization.

SUMMARY

The present invention generally relates to devices and methods for dynamically stabilizing a spinal column motion segment including at least two vertebrae.

In one form, a spinal stabilization system includes first and second anchor assemblies engageable to respective ones of first and second vertebral bodies and an elongated connecting element including opposite first and second anchor engaging portions and a length along a longitudinal axis between the first and second anchor engaging portions sized for positioning between and engaging each of said first and second anchor assemblies when the first and second anchor assemblies are engaged to the respective vertebral bodies. The connecting element further includes a support portion between the first and second anchor engaging portions. The support portion includes first and second support members spaced from one another on opposite sides of the longitudinal axis. A stabilizer member extends between and is engaged to the support members in a transverse orientation to the longitudinal axis.

In another form, a connecting element for a spinal stabilization system includes opposite end portions lying along a longitudinal axis and first and second support members diverging relative to one another from the first end portion to respective ones of first and second apexes of the first and second support members. The first and second support members further converge relative to one another toward the longitudinal axis from the respective apex to the second end portion. The connecting element also includes a stabilizer member extending between the first and second apexes.

In another form, a connecting element for a spinal stabilization system includes opposite end portions lying along a longitudinal axis that are spaced for engagement with first and second vertebral bodies of the a spinal column. The connecting element also includes a support portion providing a spring with a hoop-like form extending between the first and second anchor engaging portions and a stabilizer member extending through the support portion between opposite sides thereof in a transverse orientation to the longitudinal axis.

In yet another form, a method for stabilizing a spinal column segment comprises: engaging a first anchor to a first vertebral body of the spinal column; engaging a second anchor to a second vertebral body of the spinal column; engaging a connecting element between the first and second anchors, the connecting element including a support portion including first and second support members extending between opposite end portions of the connecting element along a longitudinal axis, the first and second support members defining a window therebetween along the longitudinal axis; and resisting movement of the first and second support members away from the longitudinal axis in response to compression of the support portion with a stabilizer member in the window.

These and other aspects will be discussed further below.

DESCRIPTION OF THE ILLUSTRATED EMBODIMENTS

Figure 1:
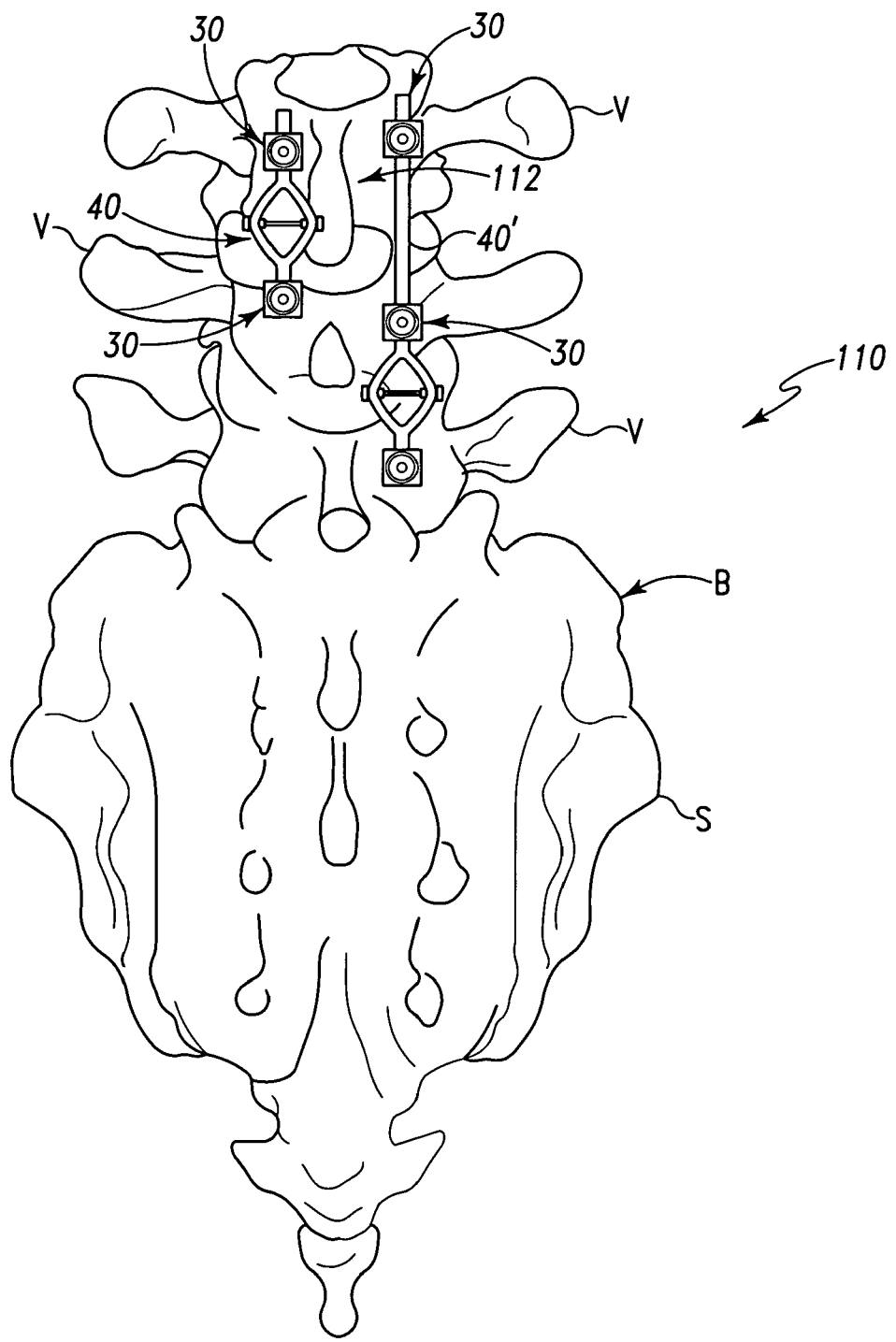
FIG. 1 is a posterior elevation view of a spinal column segment and spinal implant system.

For the purposes of promoting an understanding of the principles of the invention, reference will now be made to the embodiments illustrated in the drawings and specific language will be used to describe the same. It will nevertheless be understood that no limitation of the scope of the invention is thereby intended. Any such alterations and further modifications in the illustrated devices, and such further applications of the principles of the invention as illustrated herein are contemplated as would normally occur to one skilled in the art to which the invention relates.

Devices and methods for providing dynamic stabilization of one or more spinal motion segments are provided. The devices and methods include a connecting element between bone anchor assemblies that can be engaged to at least two vertebral bodies of a spinal motion segment. The connecting element extends along a longitudinal axis and includes end portions engageable to respective ones of the anchor assemblies and a support portion between the end portions. The support portion can include first and second support members extending along opposite sides of and laterally offset from the longitudinal axis and at least one stabilizer member extending transversely to the longitudinal axis to connect the first and second support members.

The stabilizer member can extend transversely to the longitudinal axis and engage the first and second support members at apexes of the first and second support members. The support members can form a hoop or ring type form of any shape where the apexes of the support members are offset from the longitudinal axis. The support members converge toward one another and the longitudinal axis in each of the directions from the apexes where they are joined with the respective end portion.

The anchor assemblies discussed herein can be multi-axial or uni-axial in form, and can include an anchor member engageable to a vertebral body and a receiver, post or other device for receiving or engaging a respective end portion of the connecting element. The multi-axial anchor assemblies allow the anchor member to be positioned at various angles relative to the connecting element engaging portion of the anchor assembly. The uni-axial anchor assemblies can also provide a fixed positioning of the connecting element engaging portion to the anchor member. The anchor member of the anchor assemblies can form a distal lower portion that is engageable to a vertebral body with the proximal connecting element engaging portion positioned adjacent the vertebral body. In one embodiment, the anchor member is in the form of a bone screw with a threaded shaft and a proximal head that is pivotally captured in the receiver. In other embodiments, the distal anchor member can be in the form of a hook, staple, cable, tether, suture anchor, interbody fusion implant, artificial disc implant, bolt, or other structure engageable to bony tissue. The implant engaging portion can include a receiver that defines a passage that receives the respective end portion of the connecting element therein, thereon, therethrough, or thereover, for example. The connecting element can extend from one or both of the anchor assemblies for securement to one or more additional vertebral bodies.

FIG. 1 illustrates a posterior spinal implant system 110 located along a spinal column of a patient. More specifically, implant system 110 can be affixed to bones B of the spinal column segment 112 from a posterior approach, although application in posterior-lateral, lateral, antero-lateral and anterior approaches are also contemplated. Bones B can include the sacrum S and several vertebral bodies V. Implant system 110 generally includes several bone anchor assemblies 30 and elongated connecting elements 40 and 40' structured to selectively interconnect with bone anchor assemblies 30. Connecting elements 40 may have a length sized to extend between bone anchor assemblies 30 engaged to least two vertebral bodies V. Connecting element 40' has a length sized to extend along three or more vertebrae. Connecting elements 40, 40' may be solid or hollow along some or all of its length and/or may be of homogenous or heterogeneous composition. In implant system 110, bone anchor assemblies 30 are affixed to various locations of the spinal column segment 112, such as the pedicles, and interconnected with one or more connecting elements 40, 40'. Spinal implant system 110 may be used for, but is not limited to, treatment of degenerative spondylolisthesis, fracture, dislocation, scoliosis, kyphosis, spinal tumor, and/or a failed previous fusion.

Figure 2:
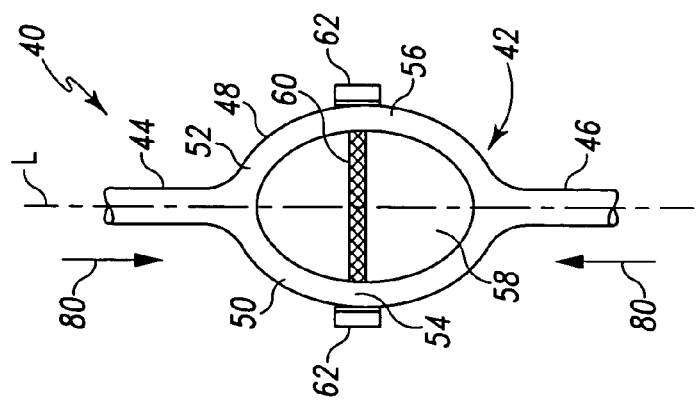
FIG. 2 is an elevation view of one embodiment connecting element of the spinal implant system of FIG. 1 in a neutral condition.

FIG. 2 shows an elevation view of one embodiment of connecting element 40, it being understood that connecting element 40' could be similarly configured. Connecting element 40 includes a body 42 extending along a longitudinal axis L between a first end portion 44 and an opposite second end portion 46. A support portion 48 extends between and connects end portions 44, 46. End portions 44, 46 can be configured to be engaged to a respective one of the bone anchor assemblies 30. In one embodiment, end portions 44, 46 are in the form of spinal rod portions with circular cross-sections orthogonally to longitudinal axis L. In another embodiment, end portions 44, 46 are each sized with a length along longitudinal axis L to extend from support portion 48 and engage an anchor assembly engaged to an adjacent vertebra. In another embodiment, one or both of the end portions 44, 46 has a length along longitudinal axis L that extends between two or more anchor assemblies engaged to two or more adjacent vertebrae, such as shown with connecting element 40'. In such embodiments, the respective end portion 44, 46 can include a cross-section that is constant between adjacent anchor assemblies, or that includes another support portion 48 between anchor assemblies.

Support portion 48 extends between end portions 44, 46 and provides a hoop-type form with first support member 50 and second support member 52. Support members 50, 52 bifurcate at the respective end portions 44, 46 and extend along and are angularly oriented relative longitudinal axis L on opposite sides thereof. Support members 50, 52 can have oppositely bowed, angular or arc shape such that each forms an apex 54, 56, respectively, at or about the mid-length of the support member along longitudinal axis L that is laterally offset from longitudinal axis L. In order to form the apexes 54, 56, support members 50, 52 diverge arcuately and/or linearly from one another and longitudinal axis L from end portion 44 toward end portion 46 to the respective apex 54, 56. Support members 50, 52 then converge arcuately and/or linearly from the respective apex 54, 56 to the opposite end portion 46.

Support portion 48 defines a window between support members 50, 52 that can have any one of a number of shapes. Window 58 can be oval, circular, diamond, polygonal, or irregular in shape in order to provide support portion 48 with a hoop-type form that provides a spring-like mechanism to facilitate flexing of support members 50, 52 transversely to longitudinal axis L in response to tension and compression loads along longitudinal axis L.

Connecting element 40 further includes a stabilizer member 60 in support portion 48 that extends between and interconnects support members 50, 52. Stabilizer member 60 extends transversely to longitudinal axis L and is engaged at opposite ends thereof to a respective one of the support members 50, 52. In one embodiment, stabilizer member 60 extends through holes in the support members 50, 52 and includes a coupling member 62 engaged to each end thereof that retains and prevents passage of the stabilizer member 60 through the respective adjacent holes in support members 50, 52.

Figure 5:
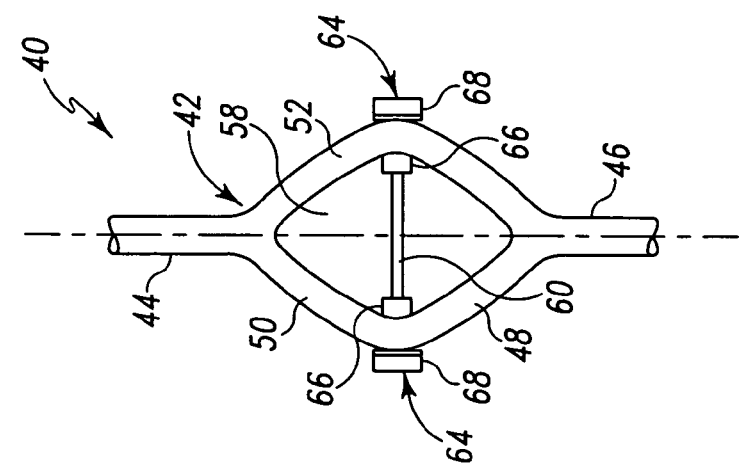
FIG. 5 is an elevation view of another embodiment connecting element in a neutral condition.

Other embodiments contemplate other devices for securing stabilizer member 60 to the respective support members 50, 52. For example, in FIG. 5 there is shown a coupling member 64 having a head 68 along the outer side of the respective support member 50, 52 and a post 66 extending through the respective support member 50, 52. The ends of stabilizer member 60 can be received in respective ones of the posts 66. Posts 66 can be crimped about the respective end of stabilizer member 60 to retain stabilizer member 60 therein.

Figure 6:
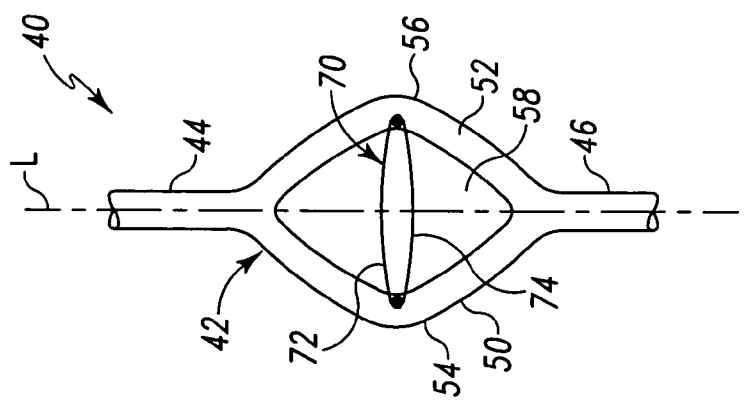
FIG. 6 is an elevation view of another embodiment connecting element in a neutral condition.

In FIG. 6, there is shown another embodiment stabilizer member 60 in the form of a belt or looped tether 70 having first and second linking portions 72, 74 extending alongside one another and between and through holes in support members 50, 52 adjacent the respective apexes 54, 56. The ends of the looped tether 70 can overlap one another and be crimped, sewn, fastened, adhered or otherwise secured to one another to maintain the looped configuration. In another embodiment, the support members 50, 52 are molded about the ends of the looped tether 70, and looped tether 70 can be a continuous type loop such as is provided by a rubber-band. In yet another embodiment, the looped tether can be received in grooves or tracks about the outer surfaces of support members 50, 52. Supplemental fixation can be provided with fasteners engaging the stabilizer member to the respective support members.

Referring back to FIG. 2, connecting element 40 is shown in a neutral condition. When engaged to the adjacent vertebral bodies in this condition, support portion 48 may be somewhat compressed in response to normal axial loads, as indicated by arrows 80, that may be exerted and required to support the adjacent vertebrae. In the neutral condition, stabilizer member 60 may not be tensioned or compressed, although slight tensioning or compression is not precluded.

Figure 3:
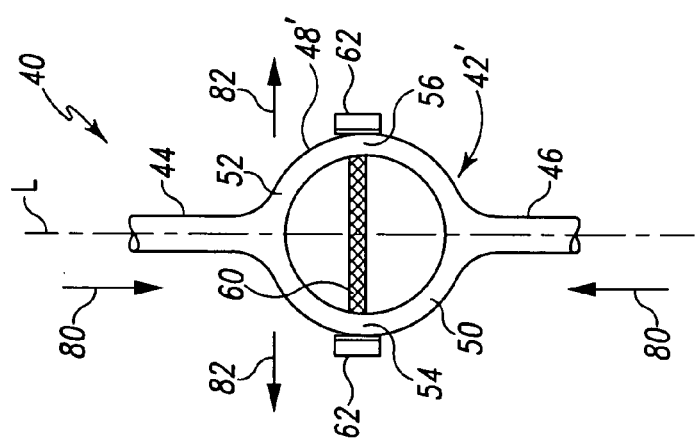
FIG. 3 is the connecting element of FIG. 2 in an active, compressed condition.

In FIG. 3, axial compressive loads 80 are sufficient to deform the connecting element 40 to a compressed condition indicated by body 42' and support portion 48'. Support members 50, 52 can be outwardly bowed or flexed, as indicated by arrows 82, such that support members 50, 52 tend to move away from longitudinal axis L and end portions 44, 46 move toward one another along longitudinal axis L. Stabilizer member 60 is tensioned and in an active condition to resist movement of support members 50, 52 away from one another and away from longitudinal axis L. Stabilizer member 60 thus resists flexing and buckling of support members 50, 52 and increases the stiffness of connecting element 40 in compression, while the laterally offset relationship of the apexes of support members 50, 52 from longitudinal axis L does provide limited movement of the spinal motion segment to which connecting element 40 is attached.

Figure 4:
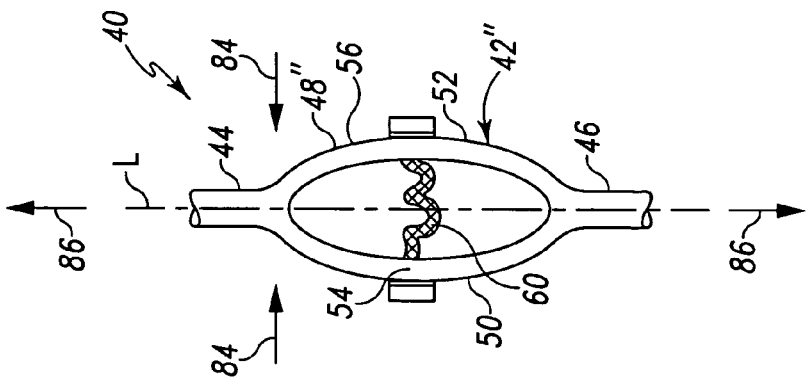
FIG. 4 is the connecting element of FIG. 2 in an active, tensioned condition.

In FIG. 4, axial tension loads 86 are exerted on connecting element 40 and tension connecting element 40 as indicated by body 42" and elongate support portion 48". The tension load can cause support members 50, 52 to straighten or flex inwardly, as indicated by arrows 84, such that support members 50, 52 tend to move toward longitudinal axis L. Stabilizer member 60 is an active condition and slackens in response to compression of it by support members 50, 52 so that movement of the support members 50, 52 toward one another and toward longitudinal axis L is not resisted by stabilizer member 60. Stabilizer member 60 thus does not increase the stiffness of connecting element 40 in tension.

Stabilizer member 60 provides connecting element 40 with an asymmetrical stiffness in compression and tension since stabilizer member 60 is activated to resist loading when support portion 48 is sufficiently compressed to flex support members 50, 52 away from one another, but slackens in response to movement of support members 50, 52 toward one another under tension loading of connecting element 40. Support portion 48 can be resilient so that it returns toward and is normally biased to return to or toward its shape in the neutral condition.

Figure 7:
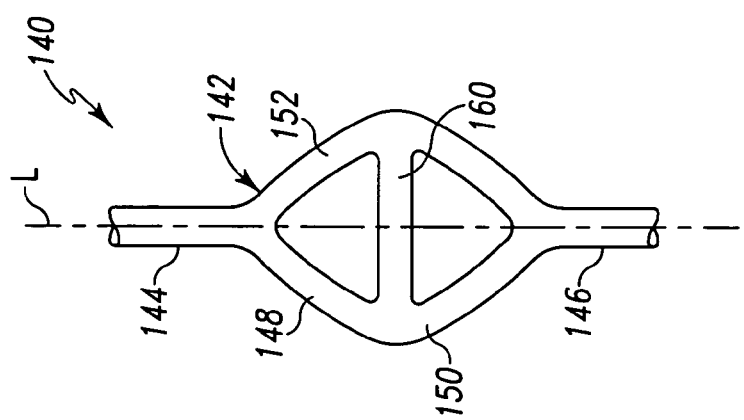
FIG. 7 is an elevation view of another embodiment connecting element in a neutral condition.

FIG. 7 shows another embodiment connecting element 140 having a body 142 extending along longitudinal axis L between end portions 144, 146. Support portion 148 extends between end portions 144, 146, and end portions 144, 146 and support portion 148 can be configured similarly to end portions 44, 46 and support portion 48 discussed above with respect to connecting element 40. Support portion 148 includes a stabilizer member 160 extending between support members 150, 152 transversely to longitudinal axis L. Stabilizer member 160 is in the form of an elongated ribbon, rod or bar with ends that form a unitary, integral connection with the respective support member 150, 152 at its respective apex.

Stabilizer member 160 can be configured to provide some resistance to movement of support members 150, 152 toward one another, but slackens or buckles when a threshold tension force is achieved. Alternatively, stabilizer member 160 can slacken and provide no resistance when activated as a result of axial tension forces.

Stabilizer members 60, 160 can provide the connecting element with a stiffness that provides less resistance to spinal motion that creates axial tension loading, yet can provide greater resistance to spinal motion that creates axial compression loading. Accordingly, spinal motion can be preserved while more effectively limiting compression or movement of the adjacent vertebral bodies toward one another, which may be less desirable in certain treatment conditions.

The connecting elements can resist motion in two directions along the longitudinal axis L while providing a differing stiffness in each of the two directions. The support portion can provide a spring-type mechanism, and the stabilizer member can increase the stiffness of the connecting element at least when the connecting element is compressed. The stabilizer member can be pliable to slacken when the connecting element is tensioned, but strong enough to resist bulging of the support portion when the connecting element is in compression. The stabilizer member and support portion cooperate to provide differing mechanical properties in differing modes of loading and/or motion of the connecting element.

Other embodiments contemplate other arrangements for the stabilizer member relative to the support members and the longitudinal axis in lieu of or in addition to the arrangements discussed above. For example, one or more additional or alternative stabilizers can extend between angled portions of the support members above and/or below any stabilizer member that extends between the apexes of the support members. In another example, a pair of stabilizers could be provided that extend diagonally relative to one another and engage the support members above and/or below the respective apexes. The diagonal stabilizer members can provide increased stiffness to resist torsional or rotational forces created by spinal rotation. In another embodiment, the stabilizer member extends along the longitudinal axis between the end portions of the connecting element to provide increased stiffness to resist axial tension forces while slackening or buckling in response to compression forces that compress the support portion between the end portions of the connecting element.

The connecting element and/or stabilizer member can be made from nitinol, titanium, stainless steel, or other biocompatible metals and alloys thereof. The connecting element and stabilizing member can also be made from PEEK or other polymer material that is biocompatible. The stabilizer member can be made from a material that is the same as or that differs from the material of the connecting element. The stabilizer member can be a rod, cord, rope, wire, tether, belt, band, ribbon, braid, suture, bar, or include any other suitable form. The stabilizer member can be unitary and integral with the connecting element, or can be a separate component attached thereto.

While the invention has been illustrated and described in detail in the drawings and foregoing description, the same is to be considered as illustrative and not restrictive in character, it being understood that all changes and modifications that come within the spirit of the invention are desired to be protected.

What is claimed is:

1. A spinal stabilization system, comprising:
first and second anchor assemblies engageable to respective ones of first and second vertebral bodies; and
an elongated connecting element including opposite first and second anchor engaging end portions and a length along a longitudinal axis between said first and second anchor engaging end portions, each of said first and second anchor engaging end portions including a spinal rod portion extending longitudinally on said longitudinal axis and said length is sized for positioning each of said spinal rod portions in a respective one of said first and second anchor assemblies on said longitudinal axis when said first and second anchor assemblies are engaged to the respective vertebral bodies, said connecting element further including a support portion between said first and second anchor engaging end portions, said longitudinal axis extending through said support portion and said support portion including first and second support members spaced from one another on opposite sides of said longitudinal axis, and further comprising at least one stabilizer member extending through aligned holes of said support members and engaged to said support members in a transverse orientation to said longitudinal axis.

2. The system of claim 1, wherein said first and second support members define a window with portions offset laterally from said longitudinal axis.

3. The system of claim 1, wherein said stabilizer member includes a flexible body extending between said support members, said flexible body slackening when compressed.

4. The system of claim 3, wherein said first and second support members move toward said longitudinal axis in response to axial tensioning of said connecting element thereby slackening said stabilizer member extending therebetween, said stabilizer member further tensioning to resist movement of said first and second support members away from said longitudinal axis in response to axial compression of said connecting element.

5. The system of claim 4, wherein said body of said stabilizer member includes opposite ends extending through said aligned holes in a respective adjacent one of the first and second support members, and further comprising coupling members at said opposite ends of said stabilizer member to retain and prevent passage of said stabilizer member through said hole in said respective adjacent support member.

6. The system of claim 5, wherein said coupling members each include a post extending through said respective support member and a head on a side of said respective support member opposite said longitudinal axis.

7. The system of claim 6, wherein each of said posts is crimped about a respective one of said opposite ends of said stabilizer member.

8. The system of claim 1, further comprising a third anchor assembly engageable to a third vertebral body and wherein one of said spinal rod portions of said elongated connecting element extends axially along a length sized to engage said one of said spinal rod portions to said third anchor assembly when said third anchor assembly is engaged to the third vertebral body.

9. The system of claim 1, wherein said first and second support members diverge from said first anchor engaging portion to respective ones of first and second apexes of said first and second support members, said first and second support members further converging toward said longitudinal axis from said respective apex to said second anchor engaging portion.

10. The system of claim 9, wherein said stabilizer member extends between said first and second apexes.

11. A spinal stabilization system, comprising:
first and second anchor assemblies engageable to respective ones of first and second vertebral bodies;
an elongated connecting element including opposite first and second anchor engaging end portions and a length along a longitudinal axis between said first and second anchor engaging end portions, each of said first and second anchor engaging end portions including a spinal rod portion extending longitudinally on said longitudinal axis and said length is sized for positioning each of said spinal rod portions in a respective one of said first and second anchor assemblies on said longitudinal axis when said first and second anchor assemblies are engaged to the respective vertebral bodies, said connecting element further including:
first and second support members between which said longitudinal axis extends and diverging relative to one another and away from said longitudinal axis from said first anchor engaging end portion to respective ones of first and second apexes of said first and second support members, said first and second support members further converging relative to one another toward said longitudinal axis from said respective apex to said second anchor engaging end portion; and
a stabilizer member extending through aligned holes of said first and second support members at a location between said first and second apexes.

12. The system of claim 11, wherein said stabilizer member is orthogonally oriented to said longitudinal axis.

13. The system of claim 11, wherein said first and second support members define a generally circular-shaped window therebetween and said stabilizer member extends through said window between said support members.

14. The system of claim 11, wherein said stabilizer member is structured to slacken when said first and second support members move toward said longitudinal axis in response to axial tensioning of said connecting element, said stabilizer member further being structured to tension to resist movement of said first and second support members away from said longitudinal axis in response to axial compression of said connecting element.

15. A spinal stabilization system, comprising:
first and second anchor assemblies engageable to respective ones of first and second vertebral bodies; and
an elongated connecting element including opposite first and second anchor engaging end portions and a length along a longitudinal axis between said first and second anchor engaging end portions, each of said first and second anchor engaging end portions including a spinal rod portion, extending longitudinally on said longitudinal axis and said length is sized for positioning each of said spinal rod portions in a respective one of said first and second anchor assemblies on said longitudinal axis when said first and second anchor assemblies are engaged to the respective vertebral bodies, said connecting element further including a support portion through which said longitudinal axis extends and providing a spring with a hoop-shaped form extending between said first and second anchor engaging end portions and a stabilizer member extending through said hoop-shaped form transversely to said longitudinal axis and said stabilizer member further extends through aligned holes in opposite sides of said support portion where said stabilizer member is engaged with opposite sides of said support portion.

16. The system of claim 15, wherein said hoop-shaped form is formed by:
first and second support members diverging relative to one another from said first anchor engaging end portion to respective ones of first and second apexes of the first and second support members, said first and second support members further converging relative to one another toward said longitudinal axis from said respective apex to said second anchor engaging end portion; and
said stabilizer member extends between and is engaged to said first and second apexes.

17. The system of claim 16, wherein said stabilizer member includes opposite ends extending through said aligned holes in respective adjacent ones of the first and second support members, and further comprising coupling members at said opposite ends of said stabilizer member to retain and prevent passage of said stabilizer member through said hole in said respective adjacent support member.

18. The system of claim 11, wherein said stabilizer member includes opposite ends extending through said aligned holes in respective adjacent ones of the first and second support members, and further comprising coupling members at said opposite ends of said stabilizer member to retain and prevent passage of said stabilizer member through said hole in said respective adjacent support member.

19. The system of claim 11, further comprising a third anchor assembly engageable to a third vertebral body and wherein one of said spinal rod portions of said elongated connecting element extends on said longitudinal axis along a second length sized to engage said one of said spinal rod portions to said third anchor assembly when said third anchor assembly is engaged to the third vertebral body.

20. The system of claim 15, further comprising a third anchor assembly engageable to a third vertebral body and wherein one of said spinal rod portions of said elongated connecting element extends on said longitudinal axis along a second length sized to engage said one of said spinal rod portions to said third anchor assembly when said third anchor assembly is engaged to the third vertebral body.

* * * * *